(12) United States Patent
Calvo et al.

(10) Patent No.: US 10,527,564 B2
(45) Date of Patent: Jan. 7, 2020

(54) METHOD FOR THE ESTIMATION OF KEROGEN MATURITY BY X-RAY PHOTOELECTRON SPECTROSCOPY

(71) Applicant: YPF Tecnologia S.A., Ciudad Autonoma de Buenos Aires (AR)

(72) Inventors: Alejandra Calvo, La Plata Pcia. de Buenos Aires (AR); Antonela Canneva, La Plata Pcia. de Buenos Aires (AR); Ivan Santiago Giordana, La Plata Pcia. de Buenos Aires (AR); Ines Lidia Labayen, Ezpeleta Pcia. de Buenos Aires (AR); Georgina Erra, La Plata Pcia. de Buenos Aires (AR)

(73) Assignee: YPF TECNOLOGIA S.A., Ciudad Autonoma de Buenos Aires (AR)

( * ) Notice: Subject to any disclaimer, the term of this patent is extended or adjusted under 35 U.S.C. 154(b) by 109 days.

(21) Appl. No.: 15/926,641

(22) Filed: Mar. 20, 2018

(65) Prior Publication Data

US 2018/0284041 A1 Oct. 4, 2018

Related U.S. Application Data

(60) Provisional application No. 62/477,692, filed on Mar. 28, 2017.

(51) Int. Cl.
*G01T 1/02* (2006.01)
*G01N 23/2273* (2018.01)
*G01N 23/2202* (2018.01)
*E21B 49/08* (2006.01)
*E21B 49/00* (2006.01)

(52) U.S. Cl.
CPC ..... *G01N 23/2273* (2013.01); *G01N 23/2202* (2013.01); *E21B 49/005* (2013.01); *E21B 49/088* (2013.01)

(58) Field of Classification Search
CPC . E21B 49/005; E21B 49/088; G01N 23/2273; G01N 23/2202
USPC .......................................................... 378/83
See application file for complete search history.

(56) References Cited

U.S. PATENT DOCUMENTS

| | | | |
|---|---|---|---|
| 7,334,889 B2* | 2/2008 | Sasaki | B41J 2/17513 347/86 |
| 8,906,690 B2 | 12/2014 | Pomerantz | |
| 2010/0161302 A1* | 6/2010 | Walters | E21B 43/00 703/12 |
| 2016/0139293 A1* | 5/2016 | Misra | G01V 3/30 702/7 |
| 2017/0031051 A1* | 2/2017 | Song | E21B 41/0092 |

\* cited by examiner

*Primary Examiner* — Kenneth J Malkowski
(74) *Attorney, Agent, or Firm* — Muncy, Geissler, Olds & Lowe, P.C.

(57) ABSTRACT

Method to estimate the kerogen maturity of a rock containing organic material by X-ray photoelectron spectroscopy (XPS). Significant changes in the XPS spectrum due to changes in C hybridization, particularly $sp^2$ hybridization, allow to quantify kerogen maturity by comparison with an already known sample.

9 Claims, 6 Drawing Sheets

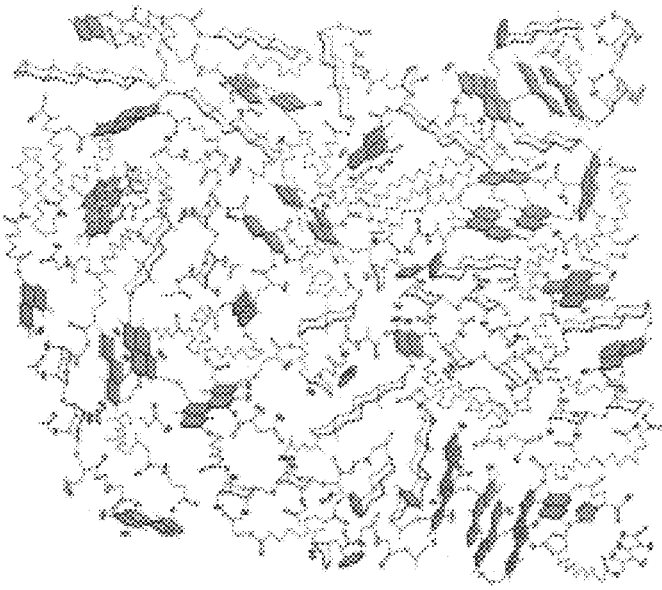
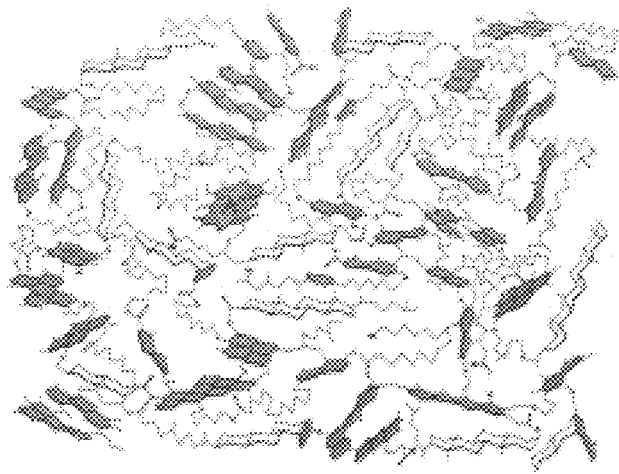
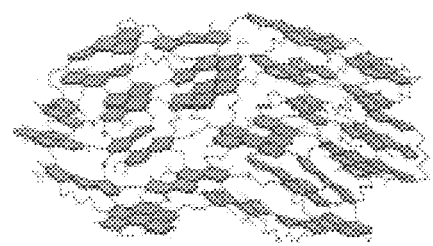
FIG. 1a

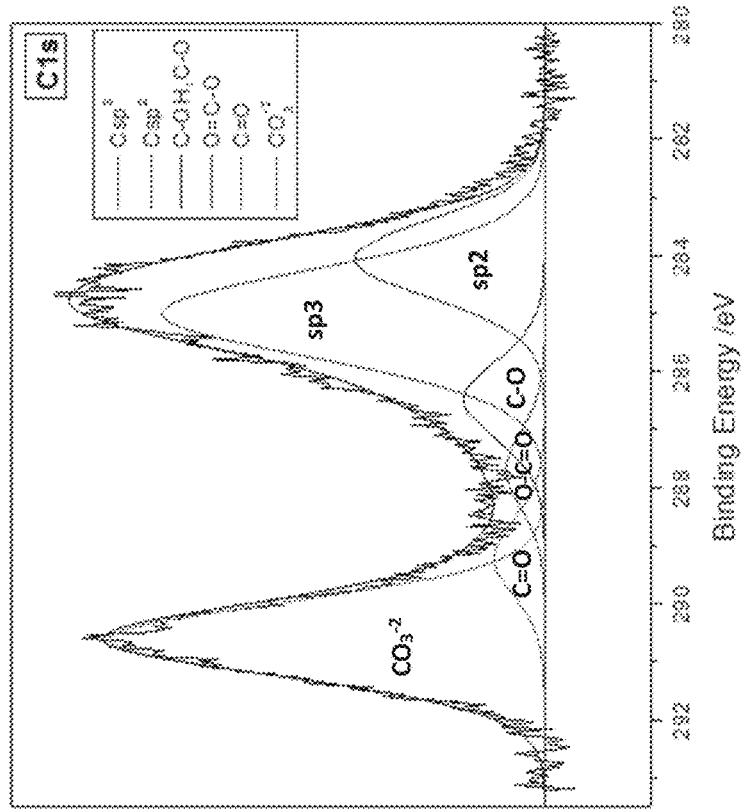
FIG. 2b $P_{c-c} = 0.24$
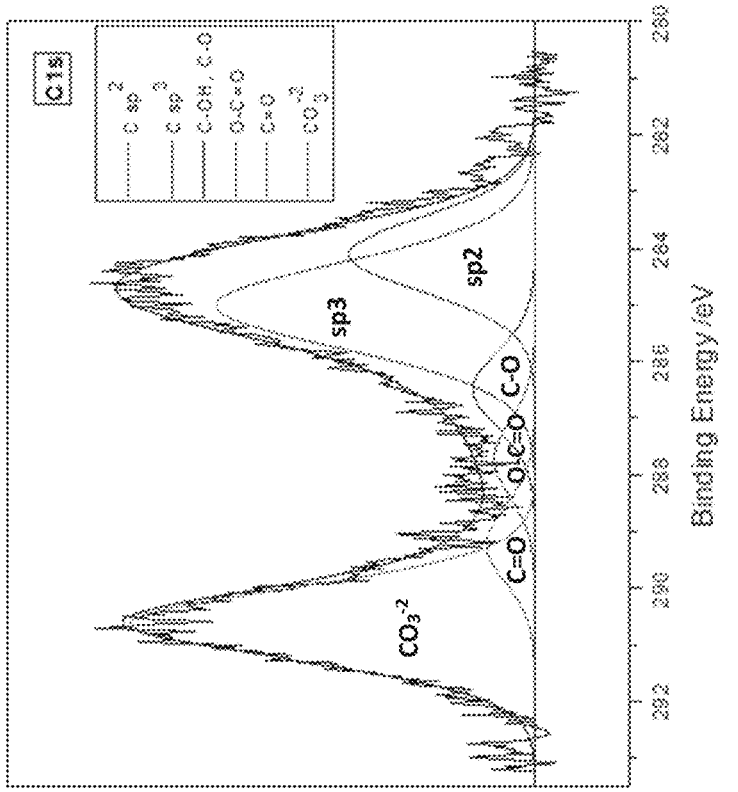
FIG. 2a $P_{c-c} = 0.26$ $P_{C-C} = 0.47$ $P_{C-C} = 0.26$

METHOD FOR THE ESTIMATION OF KEROGEN MATURITY BY X-RAY PHOTOELECTRON SPECTROSCOPY

TECHNICAL FIELD OF THE INVENTION

The present invention relates to a method for estimation of kerogen maturity useful in hydrocarbon recovery operations. In particular, the present invention relates to a method for the estimation of kerogen maturity by X-ray photoelectron spectroscopy.

BACKGROUND OF THE INVENTION

The kerogen maturity (KM), also referred to as "Level of Organic Maturity" (LOM) of a geological area is related to its hydrocarbon potential, and can therefore be used in the assessment of the commercial value of a shale reservoir.

Several experimental techniques for estimating the KM of an area are available. Traditional techniques rely on the measurement of the temperature ($T_{max}$) at which the maximum rate of hydrocarbon generation occurs in a kerogen sample during pyrolysis analysis, or the determination of vitrinite reflectance (% VR) by optical techniques.

More recent techniques are described in the scientific literature ("*Structural evolution of organic matter during maturation of coals and its impact on petroleum potential and feedstock*", Org. Geochem. 62 (2013) 17-27; *Characterization of organically Bound Oxygen Forms in Lignites. Peats and Pyrolyzed Peats by X-ray Photoelectron Spectroscopy* (XPS) *and Solid State $^{13}C$ NMR Methods, Energy& Fuels* 2002, 16, 1450-1462; "*Three-Dimensional Structure of a Huadian Oil Shale Kerogen Model: An Experimental and Theoretical Study*", Energy & Fuels 2015, 29, 4122-4136). In these works, XPS is used to analyze kerogen structure, but no quantitative determination of KM is provided. In addition, experimental essays are carried out on an isolated carbon or kerogen sample, and not directly on a shale obtained from a reservoir.

As regards the patent literature, KM is the object of the following documents:

U.S. Pat. No. 8,906,690 B2: In this patent the KM of a formation sample is determined by using Fourier Transform Infrared Spectroscopy (FTIR).

US 2016/139293 A1: In this document, a method for determining a level of organic maturity of a shale gas formation is described. The method is based on inverting multifrequency complex conductivity data to estimate volume fractions of different organic components.

There are no patent documents in the literature related to the experimental determination of KM involving XPS measurements. In addition, the available techniques for experimental determination of KM are operator dependent, time consuming and require several sample preparation steps.

There is thus a need to provide a reliable experimental method which can be directly applied to a shale, in a more operator independent manner, in order to systematize the determination of kerogen maturity.

SUMMARY OF THE INVENTION

It is an object of the present invention to provide a method to estimate the kerogen maturity of a rock containing organic material, wherein said method comprises the steps of:

a) providing a sample of the rock containing organic material to be analyzed and characterized;

b) obtaining a C1s spectrum of the rock sample by X-ray photoelectron spectroscopy;

c) calculating a parameter $P_{C-C}$ defined by equation (1)

$$P_{C-C} = \frac{A_{Csp^2}}{A_{TOC\,xps}} \quad (1)$$

where $A_{Csp^2}$ is the peak area of the region of the spectrum obtained in b) corresponding to carbon in a sp$^2$ hybridization state $A_{TOC\,xps}$ is the peak area of the region of the spectrum obtained in b) corresponding to total organic carbon; and d) determining the kerogen maturity of the rock containing organic material by comparing the value of $P_{C-C}$ to a reference value corresponding to a known kerogen maturity.

In a preferred embodiment of the method of the present invention, said rock containing organic material is a sedimentary rock. Preferably, said sedimentary rock is a shale.

In a preferred embodiment of the method of the present invention, the sample of the rock containing organic material to be analyzed and characterized is a core, cutting or outcrop sample.

In another preferred embodiment of the method of the present invention, step a) of providing a sample of the rock containing organic material to be analyzed and characterized further includes conditioning the sample. In a more preferred embodiment, the conditioning of the sample takes place inside the X-ray photoelectron spectroscopy equipment used in step b). Preferably, the conditioning of the sample comprises sputtering with argon.

In yet another embodiment of the method of the present invention, the area of the sample analyzed in step b) of obtaining a C1s spectrum of the rock sample by X-ray photoelectron spectroscopy is of about 1 mm$^2$.

In a most preferred embodiment of the method of the present invention, conditioning the sample does not include extraction, dissolution or grinding operations.

BRIEF DESCRIPTION OF THE FIGURES

FIGS. 1*a*-1*b* show a schematic representation of the principle behind the experimental method of the present invention. FIG. 1*a*: Structural representation of Type II kerogen at increasing maturity stages, corresponding to given atomic H/C or O/C ratios. Structure IIa: beginning of diagenesis; Structure IIb: beginning of catagenesis; Structure IIc: end of catagenesis, adapted from "*Kerogen origin, evolution and structure*" M. Vandenbroucke, C. Largeau Organic Geochemistry 38 (2007) 719-83; http://xpssimplified.com/elements/carbon.php). FIG. 1*b*: Significant change in the C1S spectrum of graphene with increasing maturity stages, beginning of catagenesis.

FIGS. 2*a*-2*b* show XPS spectrums evidencing the experimental reproducibility of the method of the present invention.

DETAILED DESCRIPTION OF THE INVENTION

As used herein, the term "kerogen" refers to a mixture of organic chemical compounds that make up a portion of the organic matter in a sedimentary rock. Said mixture can contain polymers formed by condensation of proteins and carbohydrates contained in organic matter, such as remains of diatoms, planktons, spores, pollen, vitrinite, etc. Alternatively, kerogen can be defined as the fraction of sedimentary organic constituent of sedimentary rocks that is insoluble in the usual organic solvents.

It is assumed herein that mature kerogen can be interpreted as comprising graphene-like structures, which contain carbon atoms with a $sp^2$ hybridization. In the course of maturation, carbon atoms in kerogen change their average hybridization from $sp^3$ to $sp^2$. Therefore, KM can be related to the amount of carbon atoms with $sp^2$ hybridization.

Figure 1B:
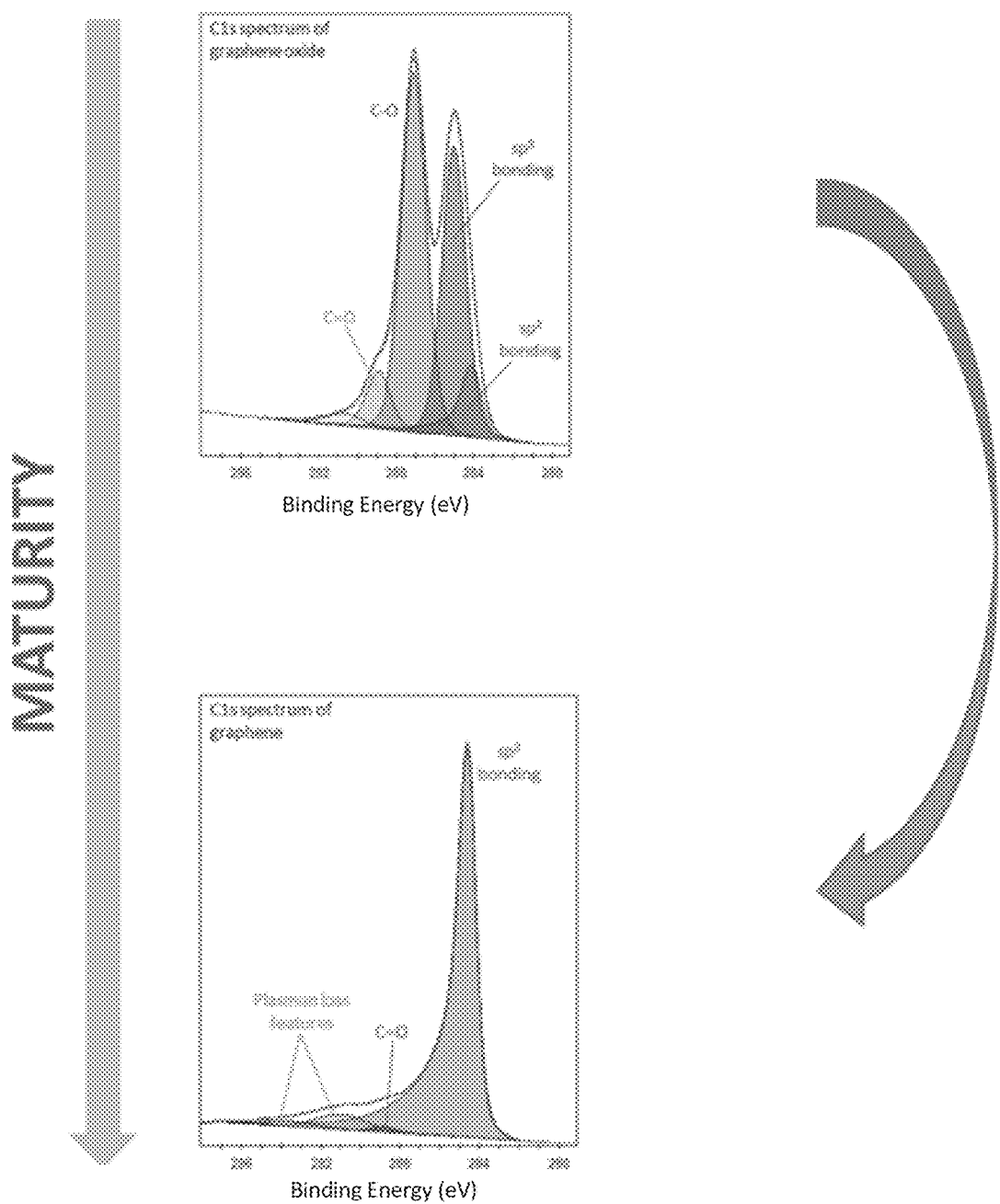

Changes in carbon atoms hybridization can be adequately quantified by X-ray photoelectron spectroscopy (XPS). Thus, this experimental technique can be used to determine kerogen maturity of a sedimentary rock sample, as illustrated in FIGS. 1a-1b. The significant changes in the XPS spectrum due to changes in C hybridization allow to quantify KM, assuming it is directly proportional to $P_{C-C}$.

As used herein, the term "C1s spectrum" refers to a section of the photoelectron spectra obtained by XPS, which ranges from 285 eV to 290 eV and is only associated to carbon species.

The term "deconvolution analysis" refers to the technique required to assess the relative amounts of the species constituting the C1s photoelectron line. The XPS C1s spectra are fitted with six peaks, corresponding to C $sp^2$, C $sp^3$, C—OH and C—O, O—C=O, C=O, and $CO_3^{-2}$.

EXAMPLES

The method of the present invention will be illustrated below with reference to the accompanying figures.

All XPS measurements disclosed in the present application were carried out with a FlexModule SPECS photoelectron spectrometer. An Al anode (1486.61 eV), a power of 100 w and a potential difference of 10 kV were used 1) Field Experiment The KM of a rock sample from Sierra de Vaca Muerta, near Zapala, Neuquén, was determined according to the method described herein. In this experiment a small sheet of rock of approximately 0.5 cm×0.5 cm×1 mm was used. The sample was introduced into the XPS equipment without any previous treatment and sputtering with Ar was carried out within the equipment. Then, in situ, the measurement of the C1s spectrum was performed for estimating the parameter Pc-c.

The resulting spectrum after C1s deconvolution analysis can be observed in FIG. 2a.

From the calculation of peak areas, the value of parameter $P_{C-C}$ was estimated at 0.26.

2) Experimental Reproducibility

The reproducibility of the experimental method was tested by a second measurement for the sample of Example 1), followed by numerical integration in order to estimate $P_{C-C}$. This experiment was carried out on the same rock portion on which the experiment of Example 1 was repeated under exactly the same conditions. The experimental results show that it is possible to obtain the parameter Pc-c in a reproducible way.

The second $P_{C-C}$ value was estimated at 0.24, in close agreement with the first value. The obtained spectrum and parameter values are shown in FIG. 2b.

3) Effect of Radiation Damage

In order to evaluate the effect of radiation damage in KM value, the same sample was subject to different X-ray irradiation time periods within the XPS equipment chamber, under the experimental conditions of Example 1).

It was determined the appearance of a bias in the estimation of the parameter Pc-c. This bias was observed only after 180 min of continuous X-ray irradiation, as a slight decrease in said parameter. After said period, the $P_{C-C}$ value was estimated at 0.19, showing a decrease from 0,24, which is consistent with a lower proportion of C atoms with $sp^2$ hybridization and therefore a lower KM value.

Figure 3B:
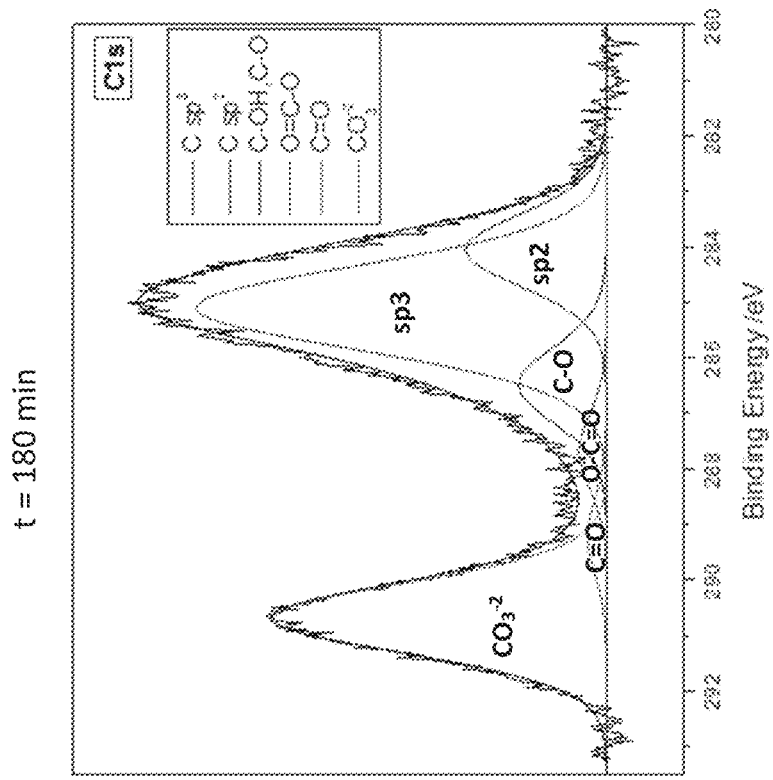
FIGS. 3*a*-3*b* show the differences in XPS spectrums and $P_{C-C}$ values due to X-ray radiation damage.
Figure 3A:
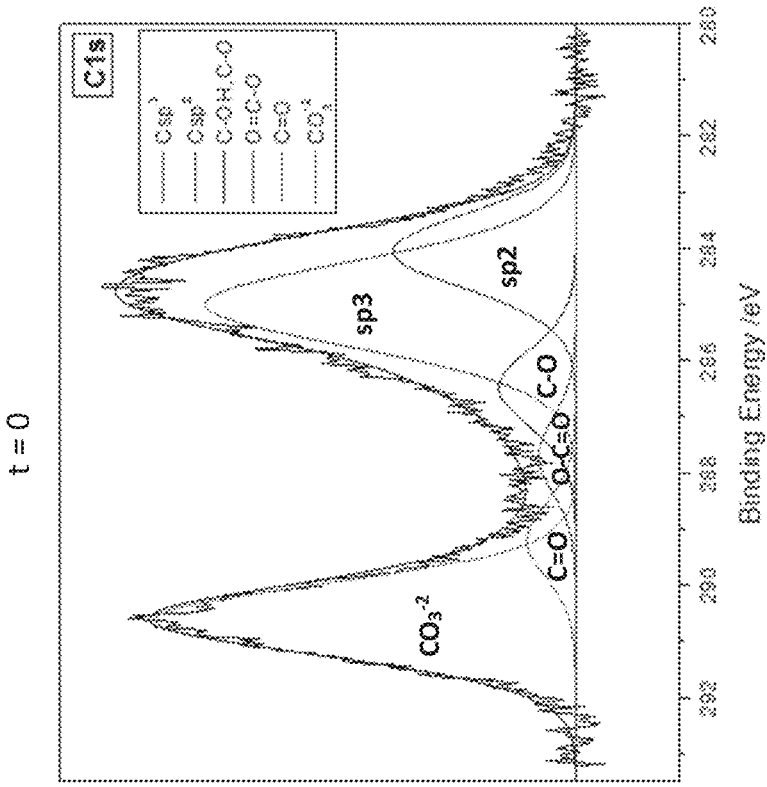

The comparative experimental results are shown in FIGS. 3a-3b.

4) Effect of Organic Matter Alteration

In order to evaluate the effect of organic matter alteration in KM value, a portion of a sample similar to that of Example 1) was subject to treatment with hydrogen peroxide, as an oxidant agent, by which the structure of the organic matter is changed.

After said treatment, the $P_{C-C}$ value was estimated at 0.47, showing an increase, which is consistent with a higher proportion of C atoms with $sp^2$ hybridization and therefore a higher KM value.

Figure 4B:
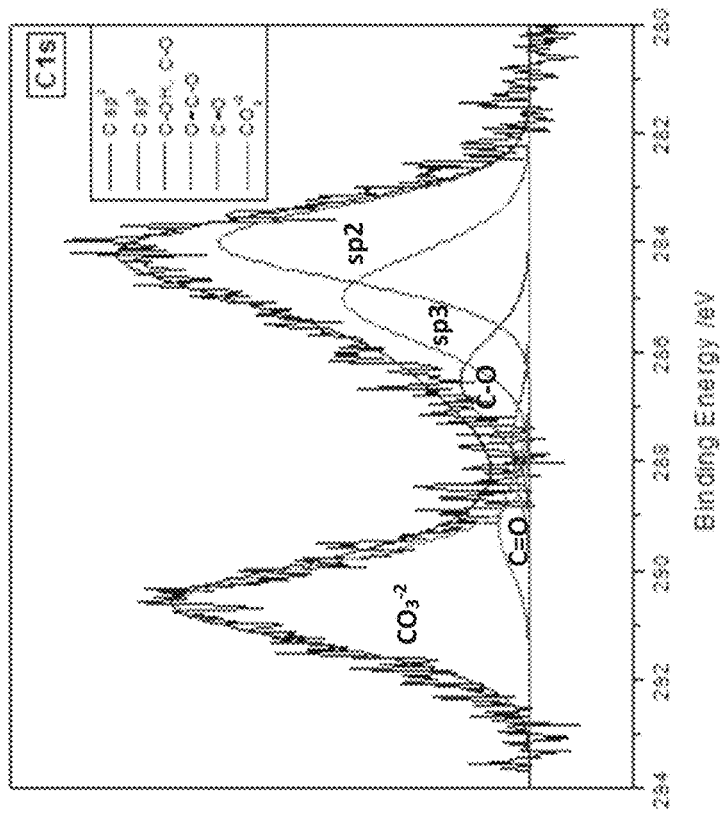
FIGS. 4*a*-4*b* show the differences in XPS spectrums due to organic matter alteration with hydrogen peroxide.
Figure 4A:
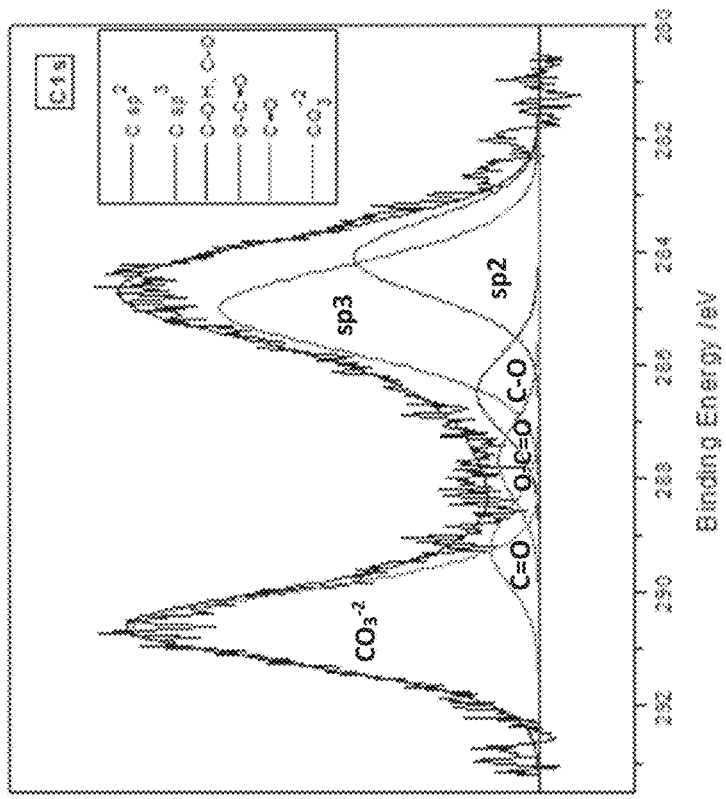

This experiment shows the sensitivity of the technique of the present invention to small changes in the C oxidation states in the kerogen, similar to those expected in the maturation process. The comparative experimental results are shown in FIGS. 4a-4b.

5) Comparison of the Parameter Pc-c Used in the Present Invention Against Known Parameters for Estimating Kerogen Maturity.

In order to validate the parameter used in the present invention (Pc-c), it was compared with two parameters that are most frequently used for estimating kerogen maturity: Vitrinite Reflectance (Ro) and the Temperature of Maximum Hydrocarbon Generation Rate during pyrolysis ($T_{max}$). The latter have limitations since they do not allow predicting maturity for all types of kerogens or for all formations.

To demonstrate the unexpected advantages provided by the present invention, two types of rocks were chosen for which the prediction of maturity can be correctly estimated by one of the two conventional parameters Ro or $T_{max}$. For this study, shale rocks from Argentine outcrops were used. Rocks containing different types of kerogens (Type I and Type II) were chosen by sampling outcrops corresponding to different formations (Cacheuta and Vaca Muerta, respectively).

Figures 5, 6:
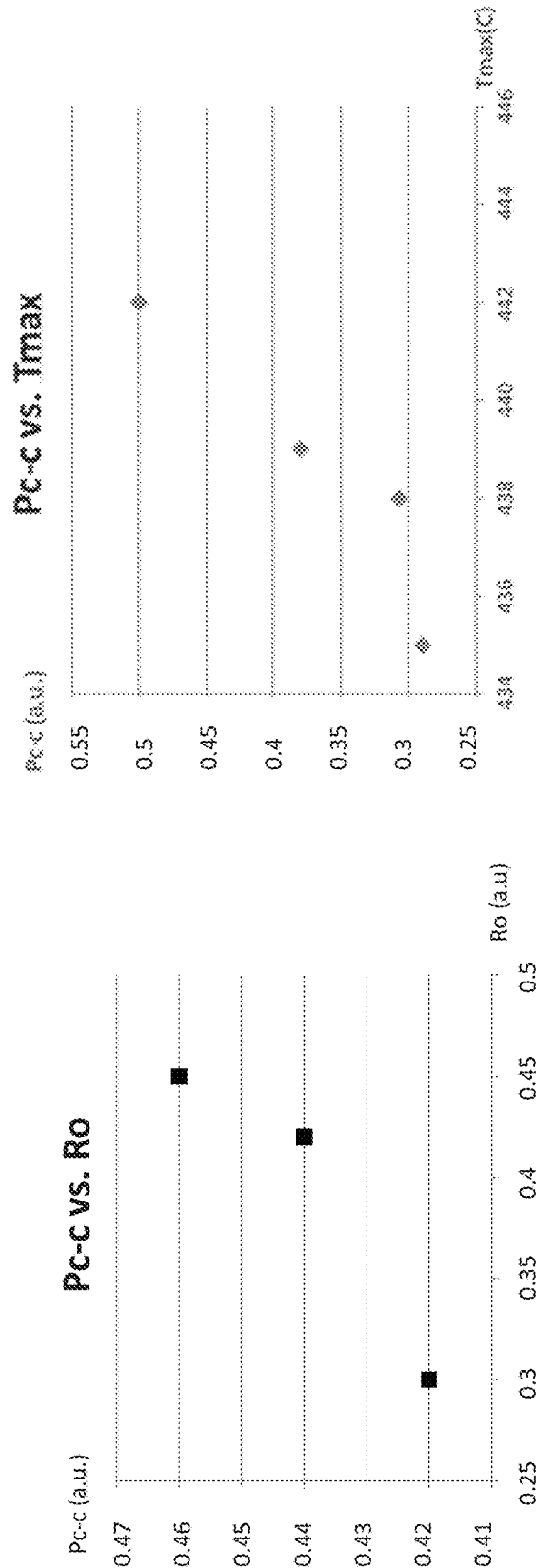
FIG. 5 shows a comparison between parameter $P_{C-C}$ used in the present invention and parameter Ro, Vitrinite Reflectance, for rocks from Cacheuta formation outcrop.
FIG. 6 shows a comparison between parameter $P_{C-C}$ used in the present invention and parameter $T_{max}$, for rocks from Vaca Muerta formation outcrop.

FIG. 5 shows the comparison of the parameter Pc-c with the parameter corresponding to the Vitrinite Reflectance (Ro), for rocks from the Cacheuta formation. This graph shows a clear correlation of the new parameter with Ro. This shows that as the maturity estimated by Ro increases, the value obtained for the parameter Pc-c measured by XPS also increases for Type I kerogens.

FIG. 6 shows the comparison of the parameter Pc-c with the parameter corresponding to the Temperature of Maximum Hydrocarbon Generation Rate during pyrolysis ($T_{max}$), for rocks from the Vaca Muerta formation. Similarly to FIG. 5, this graph shows a clear upward trend of the new parameter of the present invention. This shows that Pc-c also correlates with parameter $T_{max}$ for the prediction of maturity for Type II kerogens.

From the results shown in FIGS. 5 and 6, it can be concluded that by measuring the parameter Pc-c by the method of the present invention it is possible to estimate the kerogen maturity in an equivalent way to the estimates made by the conventional parameters (Ro and $T_{max}$). Therefore, this invention provides a technical advance regarding the previous known methods, since it is applicable independently of the type of kerogen or the origin formation of the rocks to be evaluated.

The invention claimed is:

1. A method to estimate the kerogen maturity of a rock containing organic material, wherein said method comprises the steps of:
   a) providing a sample of the rock containing organic material to be analyzed and characterized;
   b) obtaining a C1s spectrum of the rock sample by X-ray photoelectron spectroscopy;
   c) calculating a parameter $P_{C-C}$ defined by equation (1)

$$P_{C-C} = \frac{A_{Csp^2}}{A_{TOC\,xps}} \quad (1)$$

where
$A_{Csp^2}$ is the peak area of the region of the spectrum obtained in b) corresponding to carbon in a $sp^2$ hybridization state,
$A_{TOC\,xps}$ is the peak area of the region of the spectrum obtained in b) corresponding to total organic carbon; and
   d) determining the kerogen maturity of the rock containing organic material by comparing the value of $P_{C-C}$ to a reference value corresponding to a known kerogen maturity.

2. The method according to claim 1, wherein said rock containing organic material is a sedimentary rock.

3. The method according to claim 2, wherein said sedimentary rock is a shale.

4. The method according to claim 1, wherein the sample of the rock containing organic material to be analyzed and characterized is selected from a core, a cutting or an outcrop sample.

5. The method according to claim 1, where the area of the sample analyzed in step b) of obtaining a C1s spectrum of the rock sample by X-ray photoelectron spectroscopy is of about 1 mm$^2$.

6. The method according to claim 1, where step a) of providing a sample of the rock containing organic material to be analyzed and characterized further includes conditioning the sample.

7. The method according to claim 6, wherein the conditioning of the sample takes place inside the X-ray photoelectron spectroscopy equipment used in step b).

8. The method according to claim 7, wherein the conditioning of the sample comprises sputtering with argon.

9. The method according to claim 6, wherein conditioning the sample does not include extraction, dissolution or grinding operations.

* * * * *